(12) United States Patent
Shinozaki et al.

(10) Patent No.: US 9,709,496 B2
(45) Date of Patent: Jul. 18, 2017

(54) INSPECTION DEVICE FOR LIGHT-REGULATING FILM, AND PRODUCTION DEVICE FOR LIGHT-REGULATING FILM

(71) Applicant: Sharp Kabushiki Kaisha, Osaka-shi, Osaka (JP)

(72) Inventors: Daisuke Shinozaki, Osaka (JP); Yasushi Asaoka, Osaka (JP); Shohei Katsuta, Osaka (JP); Tsuyoshi Maeda, Osaka (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 14/896,762

(22) PCT Filed: May 19, 2014

(86) PCT No.: PCT/JP2014/063182
§ 371 (c)(1),
(2) Date: Dec. 8, 2015

(87) PCT Pub. No.: WO2014/199776
PCT Pub. Date: Dec. 18, 2014

(65) Prior Publication Data
US 2016/0123879 A1    May 5, 2016

(30) Foreign Application Priority Data

Jun. 10, 2013  (JP) .................................. 2013-121646

(51) Int. Cl.
*G01N 21/00* (2006.01)
*G01N 21/59* (2006.01)
(Continued)

(52) U.S. Cl.
CPC ............. *G01N 21/59* (2013.01); *G01M 11/00* (2013.01); *G01N 21/8422* (2013.01);
(Continued)

(58) Field of Classification Search
CPC ... G01M 11/00; G01N 21/59; G01N 21/8422; G01N 21/95; G01N 2201/06113;
(Continued)

(56) References Cited

U.S. PATENT DOCUMENTS

| | | | |
|---|---|---|---|
| 4,914,309 A | 4/1990 | Masaharu et al. | |
| 2014/0111862 A1 | 4/2014 | Yamamoto et al. | |

FOREIGN PATENT DOCUMENTS

| | | | |
|---|---|---|---|
| JP | 63-215953 A | 9/1988 | |
| JP | 63-295952 A | 12/1988 | |

(Continued)

OTHER PUBLICATIONS

Official Communication issued in International Patent Application No. PCT/JP2014/063182, mailed on Aug. 19, 2014.

*Primary Examiner* — Tri T Ton
(74) *Attorney, Agent, or Firm* — Keating & Bennett, LLP

(57) ABSTRACT

An inspection device of the present invention is provided with a light source unit which is disposed either one of a base material side and a light diffusing portion side and irradiates light toward a light-regulating film with respect to the light-regulating film which includes a base material, a light diffusing portion, and a light shielding layer, and a light receiver which is disposed on either the other of the base material side and the light diffusing portion side and measures an intensity of transmitted light which is emitted from the light source unit and is transmitted through the light-regulating film, and inspects a state of an inclined surface of the light diffusing portion based on a measurement result of the intensity of the transmitted light.

20 Claims, 16 Drawing Sheets

(51) Int. Cl.
    *G02B 5/02* (2006.01)
    *G01M 11/00* (2006.01)
    *G01N 21/84* (2006.01)
    *G01N 21/95* (2006.01)
    *G02F 1/1335* (2006.01)

(52) U.S. Cl.
    CPC ........... *G01N 21/95* (2013.01); *G02B 5/0231* (2013.01); *G02F 1/133504* (2013.01); *G01N 2201/062* (2013.01); *G01N 2201/06113* (2013.01)

(58) Field of Classification Search
    CPC .. G01N 2201/062; G02B 5/0231; G02B 5/00; G02B 5/02
    USPC ................. 356/432–436, 440–444, 445–448
    See application file for complete search history.

(56) References Cited

FOREIGN PATENT DOCUMENTS

| | | |
|---|---|---|
| JP | 2007-240210 A | 9/2007 |
| JP | 2008-246864 A | 10/2008 |
| JP | 2010-112803 A | 5/2010 |
| JP | 2011-64759 A | 3/2011 |
| JP | 2012-141592 A | 7/2012 |
| WO | 2012/081410 A1 | 6/2012 |
| WO | 2012/157512 A1 | 11/2012 |
| WO | 2013/061907 A1 | 5/2013 |

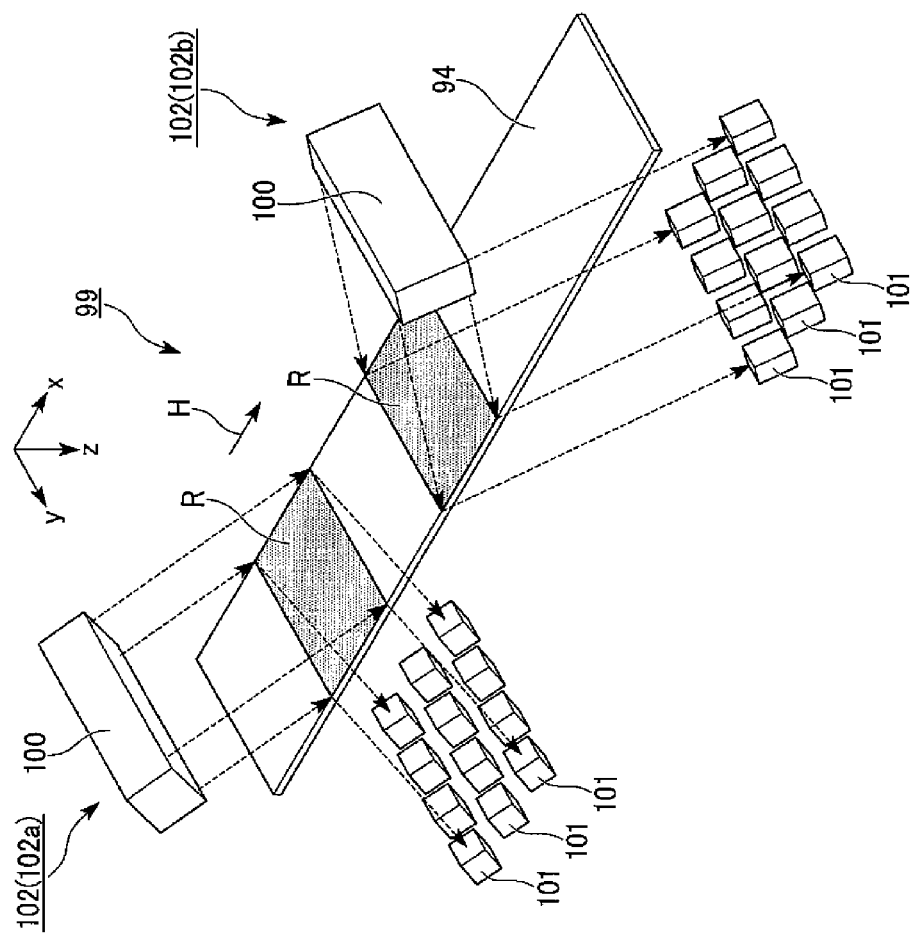

INSPECTION DEVICE FOR LIGHT-REGULATING FILM, AND PRODUCTION DEVICE FOR LIGHT-REGULATING FILM

TECHNICAL FIELD

The present invention relates to an inspection device for a light-regulating film and a production device for a light-regulating film.

The present application claims priority based on Japanese Patent Application No. 2013-121646 which was filed in Japan on Jun. 10, 2013 and contents thereof are incorporated herein.

BACKGROUND ART

A liquid crystal display device is widely used as a display of a portable electronic device including a portable telephone, or a television, a personal computer, and the like. However, it has been conventionally known that a liquid crystal display device has a narrow viewing angle while having excellent visibility from the front, in general. Therefore, various kinds of ideas to widen a viewing angle have been provided. As one of the ideas, there is the configuration in which a member for diffusing light which is emitted from a display body such as a liquid crystal panel is provided on a visual observation side of the display body.

For example, a light-regulating film which includes a transparent base material, a light diffusing portion which is formed on one surface of the transparent base material and includes a taper-shaped reflection surface, and a light shielding portion which is formed in a region other than a forming region of the light diffusing portion in one surface of the transparent base material is disclosed in PTL 1 below. In the light-regulating film, incident light is reflected on the taper-shaped reflection surface of the light diffusing portion so as to widen a diffusing angle of transmitted light more than that before incidence.

CITATION LIST

Patent Literature

PTL 1: International Publication No. 2012/081410

SUMMARY OF INVENTION

Technical Problem

A light diffusing property of a light-regulating film is largely affected by workmanship of a light diffusing portion. That is, in order to obtain a desired light diffusing property, it is important that a light diffusing portion is completed to have a shape and dimensions following the original design. However, in order to confirm a forming state of a light diffusing portion, such method is generally employed that a light-regulating film is cut and a cross-sectional shape is observed by using a microscope or the like. Therefore, there has been a problem in which inspection of a light diffusing portion takes labor and time. Further, there has been a problem in which it is difficult to accurately inspect a forming state of a light diffusing portion because the light diffusing portion is sometimes damaged when the light-regulating film is cut.

One aspect of the present invention is provided to solve the above-mentioned problems and one object is to provide an inspection device for a light-regulating film which is capable of reducing labor and time required for inspection of a light diffusing portion and is capable of inspecting a forming state of the light diffusing portion more accurately. In another aspect of the present invention, another object is to provide a production device for a light-regulating film which is capable of reducing labor and time required for inspection of a light diffusing portion and is capable of producing a light-regulating film while inspecting a forming state of the light diffusing portion more accurately.

Solution to Problem

In order to achieve the above-mentioned objects, an inspection device for a light-regulating film according to one aspect of the present invention includes a light source unit which is disposed on either one of a base material side and a light diffusing portion side and radiates light toward the light-regulating film with respect to the light-regulating film, which includes the base material having a light transmitting property, the light diffusing portion which is provided on a first surface of the base material, and a light shielding portion which is provided in a region other than a forming region of the light diffusing portion in the first surface, in which the light diffusing portion includes a light emitting end surface which is positioned on the base material side, a light incident end surface which is positioned on a side opposite to the base material and has an area larger than an area of the light emitting end surface, and an inclined surface which is inclined with respect to the light emitting end surface, and in which a height from the light incident end surface to the light emitting end surface of the light diffusing portion is larger than a layer thickness of the light shielding portion, and a light measurement means which is disposed on either the other of the base material side and the light diffusing portion side and measures an intensity of transmitted light which is emitted from the light source unit and is transmitted through the light-regulating film, in which a state of the inclined surface is inspected based on a measurement result of the intensity of the transmitted light.

In the inspection device for a light-regulating film according to one aspect of the present invention, the light measurement means may be disposed in a surface of a light incident surface of light which is incident on the light-regulating film from the light source unit and may measure a polar angle of a central axis of the transmitted light an intensity of which is the highest in the surface.

In the inspection device for a light-regulating film according to one aspect of the present invention, the light measurement means may derive an inclination angle of the inclined surface with respect to the light incident end surface based on the polar angle of the central axis of the transmitted light.

In the inspection device for a light-regulating film according to one aspect of the present invention, the light measurement means may be capable of moving within a range in which a polar angle $\theta$ made by a normal line direction of a light receiving surface of the light measurement means and a normal line direction of the base material satisfies $0° \leq \theta \leq 90°$.

In the inspection device for a light-regulating film according to one aspect of the present invention, the light measurement means may be capable of moving in an azimuth angle direction viewed from a normal line direction of a principal surface of the base material.

In the inspection device for a light-regulating film according to one aspect of the present invention, the light source unit may be capable of moving.

In the inspection device for a light-regulating film according to one aspect of the present invention, the light source unit may be capable of moving in a manner to be linked with movement of the light measurement means.

In the inspection device for a light-regulating film according to one aspect of the present invention, the light measurement means may be fixed on a position on which a polar angle θ made by the normal line direction of the light receiving surface of the light measurement means and the normal line direction of the base material becomes a specific angle within a range of $0° \leq \theta \leq 90°$.

The inspection device for a light-regulating film according to one aspect of the present invention may include a conveying means which moves the light-regulating film in a direction parallel to the principal surface of the base material.

In the inspection device for a light-regulating film according to one aspect of the present invention, the light source unit may include a plurality of light sources which are arranged with an interval in a direction orthogonal to a moving direction of the light-regulating film moved by the conveying means.

In the inspection device for a light-regulating film according to one aspect of the present invention, the light source unit may include a plurality of light sources which are arranged with an interval in a direction parallel to the moving direction of the light-regulating film moved by the conveying means.

In the inspection device for a light-regulating film according to one aspect of the present invention, the light measurement means may include a plurality of light receivers which are provided in a manner to be associated with a plurality of light sources which are arranged with an interval in a direction parallel to the moving direction.

In the inspection device for a light-regulating film according to one aspect of the present invention, the light source unit may include a linear light source which emits linear light which extends in a direction orthogonal to the moving direction of the light-regulating film moved by the conveying means.

In the inspection device for a light-regulating film according to one aspect of the present invention, the light source unit may include a planar light source.

In the inspection device for a light-regulating film according to one aspect of the present invention, the light measurement means may include a positional information acquisition means which acquires positional information of a defective part, which is detected in a case where an intensity of the transmitted light is measured, of the light-regulating film.

In the inspection device for a light-regulating film according to one aspect of the present invention, the light source unit may be configured to be disposed on the light diffusing portion side and make light incident on the light-regulating film from the light diffusing portion side.

In the inspection device for a light-regulating film according to one aspect of the present invention, the light source unit may be configured to be disposed on the base material side and make light incident on the light-regulating film from the base material side.

In the inspection device for a light-regulating film according to one aspect of the present invention, such configuration may be employed that a wavelength of light emitted from the light source unit is 550 nm, and the light measurement means detects a Y value of transmitted light which is transmitted through the light-regulating film.

In the inspection device for a light-regulating film according to one aspect of the present invention, the light source unit may be a high directivity light source.

An inspection method for a light-regulating film according to one aspect of the present invention includes radiating light from either one of a base material side and a light diffusing portion side with respect to the light-regulating film, which includes the base material having a light transmitting property, the light diffusing portion which is provided on a first surface of the base material, and a light shielding portion which is provided in a region other than a forming region of the light diffusing portion in the first surface, in which the light diffusing portion includes a light emitting end surface which is positioned on the base material side, a light incident end surface which is positioned on a side opposite to the base material and has an area larger than an area of the light emitting end surface, and an inclined surface which is inclined with respect to the light emitting end surface, and in which a height from the light incident end surface to the light emitting end surface of the light diffusing portion is larger than a layer thickness of the light shielding portion, measuring an intensity of transmitted light which is transmitted through the light-regulating film on either the other of the base material side and the light diffusing portion side, and inspecting a state of the inclined surface based on a measurement result of the intensity of the transmitted light.

A production device for a light-regulating film according to one aspect of the present invention includes the inspection device for a light-regulating film according to one aspect of the present invention.

The production device for a light-regulating film according to one aspect of the present invention may include a plurality of processing devices which respectively perform mutually-different processing, and a conveying device which conveys the light-regulating film in a middle of production among the plurality of processing devices, in which the inspection device may be disposed in a middle of a conveying path of the light-regulating film in the conveying device.

In the production device for a light-regulating film according to one aspect of the present invention, such configuration may be employed that the plurality of processing devices include an exposure device which is used for forming the light diffusing portion which is made of photosensitive resin, and an inspection result, which is obtained by the inspection device, of the inclined surface is fed back to an exposure amount of the exposure device.

Advantageous Effects of Invention

According to one aspect of the present invention, an inspection device for a light-regulating film which is capable of reducing labor and time required for inspection of a light diffusing portion and is capable of inspecting a forming state of the light diffusing portion more accurately can be provided. According to another aspect of the present invention, a method for inspecting a light-regulating film by which labor and time required for inspection of a light diffusing portion can be reduced and a forming state of the light diffusing portion can be more accurately inspected can be provided. According to still another aspect of the present invention, a production device for a light-regulating film which is capable of producing a light-regulating film having an excellent quality without lowering productivity along with inspection of the light diffusing portion can be provided.

BRIEF DESCRIPTION OF DRAWINGS

FIG. 17 is a perspective view illustrating the inspection device which is incorporated into a production device according to a ninth embodiment.

DESCRIPTION OF EMBODIMENTS

First Embodiment

A first embodiment of the present invention is described below with reference to FIG. 1 to FIG. 4.

An example of an inspection device for a light-regulating film is described in the first embodiment.

Here, in all drawings used below, reduction scales of dimensions of constituent elements may be different from each other so as to facilitate visualization of respective constituent elements.

A light-regulating film 1 which is an inspection object is first described in detail.

Figure 1:
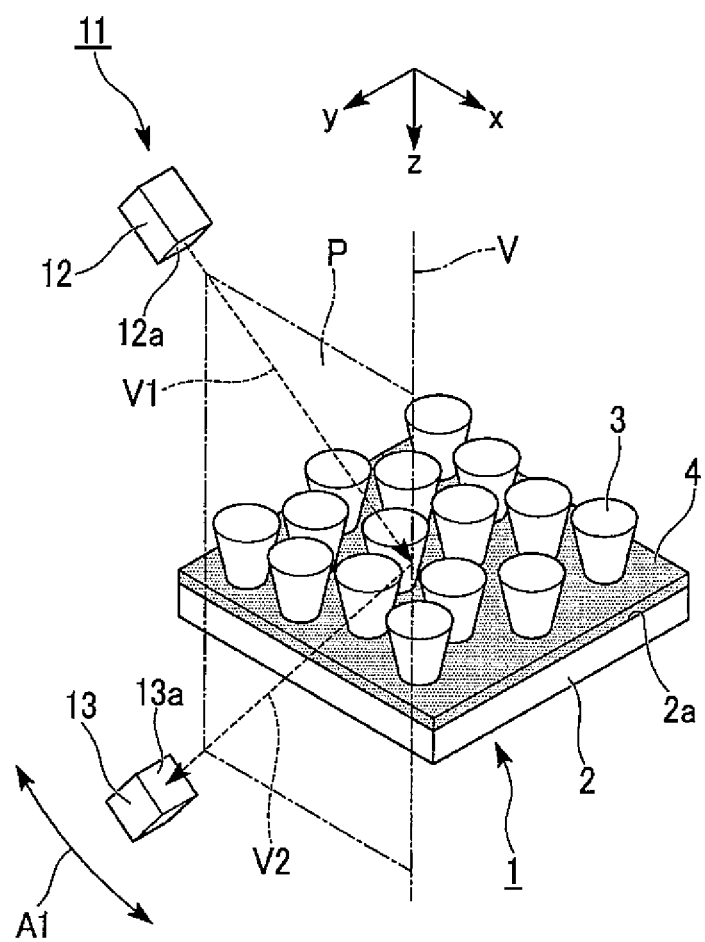
FIG. 1 is a perspective view illustrating an inspection device for a light-regulating film according to a first embodiment.

The light-regulating film 1 is composed of a base material 2, a plurality of light diffusing portions 3 which are formed on a first surface 2a of the base material 2, and a light shielding layer 4 (light shielding portion) which is formed on the first surface 2a of the base material 2, as illustrated in FIG. 1.

As the base material 2, a base material which is made of transparent resin such as a triacetyl cellulose (TAC) film, polyethylene terephthalate (PET), polycarbonate (PC), polyethylene naphthalate (PEN), and a polyether sulfone (PES) film is preferably used. The base material 2 is a base for later applied materials of the light shielding layer 4 and the light diffusing portion 3 in a production process and is required to have heat resistance and mechanical strength in a thermal treatment process in the production process. Accordingly, as the base material 2, a base material made of glass or the like may be used other than a base material made of resin.

Figure 4:
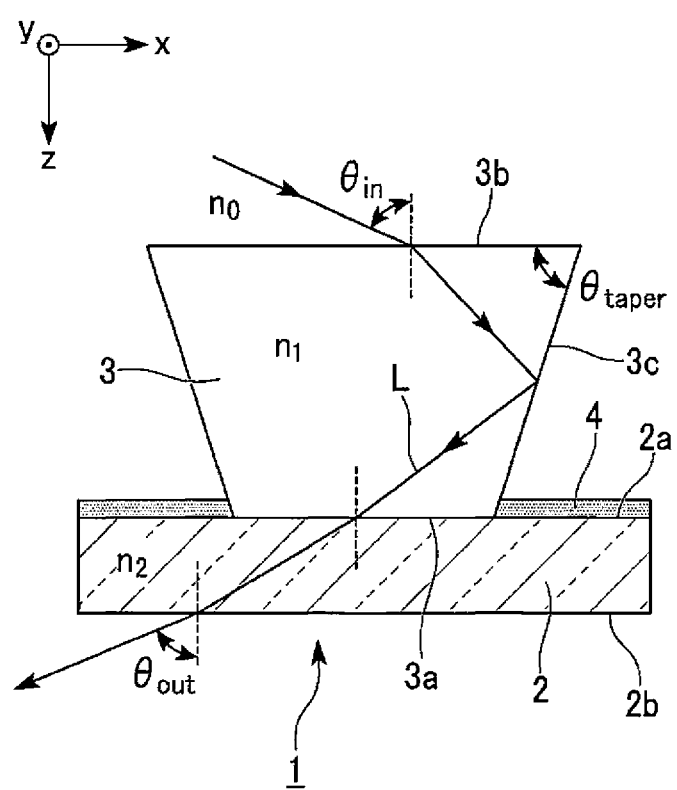
FIG. 4 is a sectional view illustrating a state of reflection in the light-regulating film.

The light diffusing portion 3 is made of an organic material, which has a light transmitting property and photosensitivity, such as acrylic resin and epoxy resin. As illustrated in FIG. 4, the light diffusing portion 3 is configured such that a shape of a horizontal section (xy section) is circular, a surface 3a which is on a base material 2 side and is a light emitting end surface is smaller, a surface 3b on a side opposed to the base material 2 and is a light incident end surface is larger, and an area of the horizontal section is gradually increased from the base material 2 side to the side opposed to the base material 2. That is, the light diffusing portion 3 has a so-called reverse-tapered circular truncated cone shape when viewed from the base material 2 side.

The light diffusing portion 3 is a portion which contributes to transmission of light in the light-regulating film 1. That is, light L incident on the light diffusing portion 3 is guided in a manner to be approximately sealed in the inside of the light diffusing portion 3 while totally reflecting on a tapered inclined surface 3c of the light diffusing portion 3, and emitted. A plurality of light diffusing portions 3 are arranged at random when viewed from a normal line direction of a principal surface of the base material 2.

For example, when the light-regulating film 1 is bonded on a display, arrangement is performed such that the base material 2 faces a visual observation side (observer side) and the light diffusing portion 3 faces a display side. Therefore, between two counter surfaces of the light diffusing portion 3 which has a circular truncated cone shape, a surface having a smaller area is the light emitting end surface 3a and a surface having a larger area is the light incident end surface 3b. An inclination angle θtaper of the inclined surface 3c of the light diffusing portion 3 (an angle made by the light incident end surface 3b and the inclined surface 3c) is approximately 80° to 85°, for example. However, the inclination angle θtaper may be an angle by which light can be sufficiently diffused when the light is emitted from the light-regulating film 1 and the inclination angle θtaper is not especially limited.

The light shielding layer 4 is formed in a region other than a forming region of a plurality of light diffusing portions 3 in the first surface 2a of the base material 2. The light shielding layer 4 is made of an organic material which has a light absorptive property and photosensitivity such as a black resist and a black ink, for example. Alternatively, a metal film such as a multi-layer film of chrome (Cr) or Cr/Cr oxide may be used. The layer thickness of the light shielding layer 4 is set to be smaller than the height from the light incident end surface 3b to the light emitting end surface 3a of the light diffusing portion 3. In the case of the present embodiment, the layer thickness of the light shielding layer 4 is approximately 150 nm, for example, and the height from the light incident end surface 3b to the light emitting end surface 3a of the light diffusing portion 3 is approximately 25 μm, for example. In a space among a plurality of light diffusing portion 3, the light shielding layer 4 exists in a portion which contacts with the first surface 2a of the base material 2 and air exists in other portions.

Here, it is preferable that a refractive index of the base material 2 and a refractive index of the light diffusing portion 3 be approximately equivalent to each other. This is because if the refractive index of the base material 2 and the refractive index of the light diffusing portion 3 are largely different from each other, such defects that a desired viewing angle cannot be obtained and the light quantity of emitted light is reduced may arise due to an occurrence of unwanted light refraction or reflection in an interface between the light diffusing portion 3 and the base material 2 when light incident from the light incident end surface 3b is to be emitted from the light diffusing portion 3, for example.

In the case of the present embodiment, air exists between adjacent light diffusing portions 3. Therefore, if the light diffusing portions 3 are made of transparent acrylic resin, for example, the inclined surface 3c of the light diffusing portion 3 is an interface between the transparent acrylic resin and air. The periphery of the light diffusing portions 3 may be filled with another material having a low refractive index. However, the refractive index difference on an interface between the inside and the outside of the light diffusing portion 3 reaches the maximum in a case where air exists in the outside among cases where any materials having a low refractive index exist. Accordingly, a critical angle is the smallest and an incident angle range in which light totally reflects on the inclined surface 3c of the light diffusing portion 3 is the largest in accordance with the Snell's law in the configuration of the present embodiment. Consequently, a loss of light is more suppressed and high brightness can be obtained.

An inspection device 11 of the light-regulating film 1 is now described. In the following description, the inspection device 11 for the light-regulating film 1 is merely referred to as the "inspection device 11".

As illustrated in FIG. 1, the inspection device 11 includes a light source unit 12 and a light receiver 13. The light source unit 12 is disposed on the light diffusing portion 3 side of the light-regulating film 1 and radiates light toward the light-regulating film 1. The light receiver 13 is disposed on the base material 2 side of the light-regulating film 1 and measures the intensity of transmitted light which is emitted from the light source unit 12 and transmitted through the light-regulating film 1. The light receiver 13 corresponds to a light measurement means in Claims. The inspection device 11 inspects a state of the inclined surface 3c of the light diffusing portion 3 based on a measurement result of the intensity of transmitted light obtained by the light receiver 13.

The light source unit 12 is provided with a light emitting diode (hereinafter, abbreviated to an LED) and a reflector composed of a concave mirror, for example. As the LED, a green LED which emits green light of a wavelength λ=550 nm, for example, is used. The LED does not especially have to have directivity. The reflector has a quadric surface shape which has a focal point, such as a parabolic shape and a paraboloidal surface shape. A position of a light emitting surface of the LED is approximately accorded with a position of the focal point of the reflector. The reflector reflects light from the LED and emits the light in a single direction.

The position of the light emitting surface of the LED is accorded with the focal point of the reflector, so that light which is emitted from the LED travels in a direction parallel to an optical axis of the reflector after reflected at the reflector even if the emitted light is incident on the reflector at any angle. Accordingly, diffused light immediately after emitted from the LED is converted into parallelized light, that is, light having high directivity by being reflected at the reflector, and emitted. Thus, the light source unit 12 is preferably a high directivity light source. Based on such perspective, a laser light source may be used as the light source unit 12, for example. The light source unit 12 is a point light source which irradiates a single point in a spot shape on the light-regulating film 1.

The light receiver 13 detects a Y value of transmitted light which is transmitted through the light-regulating film 1. As the light receiver 13, a general light receiving sensor or the like can be used. When a virtual plain surface P including a normal line V of the light-regulating film 1 is considered, the light source unit 12 and the light receiver 13 are disposed such that a normal line V1 of a light emitting surface 12a of the light source unit 12 (the optical axis of the light source unit 12) and a normal line V2 of a light incident surface 13a of the light receiver 13 (the optical axis of the light receiver 13) are positioned within one virtual plain surface P which is orthogonal to a principal surface of the light-regulating film 1. In other words, the light receiver 13 is disposed within a surface of a light incident surface of light which is incident on the light-regulating film 1 from the light source unit 12.

Figure 2:
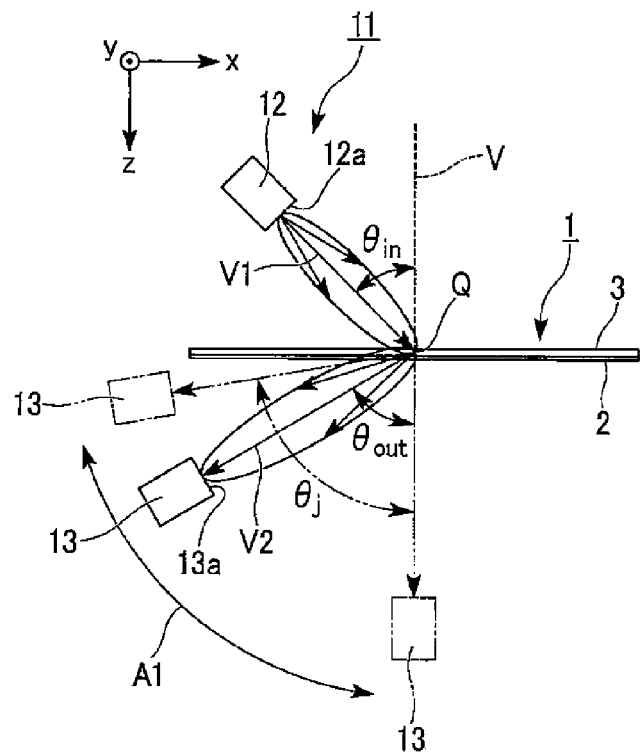
FIG. 2 is a lateral view for explaining an operation of the inspection device.

As illustrated in FIG. 2, the light receiver 13 has such configuration that the light receiver 13 can move in a polar angle direction illustrated by an arrow A1 so that the normal line V2 of the light incident surface 13a always passes through a center Q of an irradiation region of light emitted from the light source unit 12 while the light receiver 13 keeps the above-mentioned positional relation with respect to the light source unit 12. The light receiver 13 is configured to be capable of moving within a range of an angle θj, which is made by the normal line V2 of the light incident surface 13a and the normal line V of the light-regulating film 1, of 0°≤θj<90°. The angle θj which is made by the normal line V of the light-regulating film 1 and the normal line V2 of the light incident surface 13a of the light receiver 13 varies along with movement of the light receiver 13.

The inspection device 11 is provided with a control unit (not illustrated) which controls the light source unit 12 and the light receiver 13. The control unit has a function to obtain intensity distribution based on measurement results, which are obtained from the light receiver 13, of light intensities and further to calculate an inclination angle θtaper of the inclined surface 3c of the light diffusing portion 3 in the light-regulating film 1 as well as to control operations of the light source unit 12 and the light receiver 13. The inspection device 11 calculates the inclination angle θtaper of the inclined surface 3c of the light diffusing portion 3 in the light-regulating film 1 and inspects whether or not the light diffusing portion 3 which has a desired shape is produced.

A calculation procedure of the inclination angle θtaper is described.

As illustrated in FIG. 2 and FIG. 4, the light source unit 12 irradiates the light-regulating film 1 with the light L, toward a surface, on which the light diffusing portions 3 are formed, of the light-regulating film 1 by an incident angle which is inclined by a polar angle θin with respect to the normal line V of the light-regulating film 1. In other words, an angle made by the normal line V of the light-regulating film 1 and an optical axis of incident light (the normal line V1 of the light emitting surface 12a of the light source unit 12) is the incident angle θin. The light L is refracted on the light incident surface 3b of the light diffusing portion 3 to be incident on the light diffusing portion 3. The light L incident on the light diffusing portion 3 is totally reflected at the inclined surface 3c.

The light L which is totally reflected at the inclined surface 3c of the light diffusing portion 3 is refracted on the first surface 2a of the base material 2 to be incident on the base material 2. The light L incident on the base material 2 is refracted at a second surface 2b of the base material 2 to be emitted to an external space at an emitting angle which is inclined by the polar angle θout with respect to the normal line V of the light-regulating film 1. In other words, an angle made by the normal line V of the light-regulating film 1 and a central axis of transmitted light (the normal line V2 of the light incident surface 13a of the light receiver 13) is the emitting angle θout. The light receiver 13 measures an intensity of transmitted light in each polar angle while moving in the polar angle direction. The light receiver 13 acquires intensity distribution in a polar angle in a predetermined range based on measurement values of intensities of transmitted light in respective polar angles.

Figure 3:
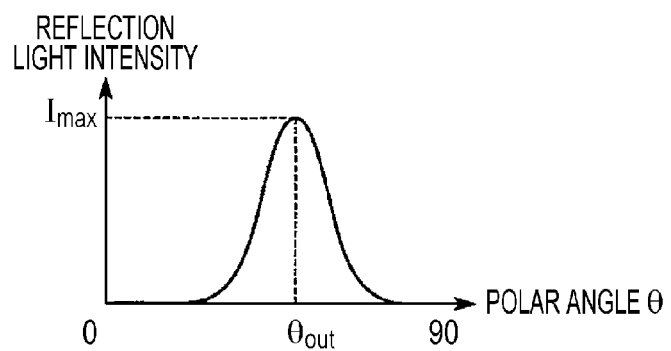
FIG. 3 is a drawing illustrating intensity distribution of reflection light in the light-regulating film.

FIG. 3 is an example of an intensity distribution curve, which is obtained from measurement results of the light receiver 13, of transmitted light. When the incident angle θin of light incident on the light-regulating film 1 from the light source unit 12 is kept constant and the light receiver 13 is moved in the polar angle direction, an intensity distribution curve illustrated in FIG. 3 is obtained. The emitting angle θout at which the intensity of transmitted light has the maximum value Imax is obtained from the intensity distribution curve.

In FIG. 4, a refractive index of the periphery of the light-regulating film 1 is denoted as $n_0$, a refractive index of the light diffusing portion 3 is denoted as $n_1$, and a refractive index of the base material 2 is denoted as $n_2$. In light of refraction at the light incident end surface 3b of the light diffusing portion 3, reflection at the inclined surface 3c of the light diffusing portion 3, refraction at the interface between the light diffusing portion 3 and the base material 2, and refraction at the light emitting surface 2b of the base material 2, the following formula (1) is derived by using the Snell's law. In accordance with the formula (1), the inclination angle θtaper of the inclined surface 3c is obtained. Here, a medium of the refractive index $n_2$, that is, the light-regulating film 1 is a parallel plain plate, so that light is merely transmitted through the light-regulating film 1 and the light-regulating film 1 does not affect an angle of emitted light. Accordingly, in the formula (1) for obtaining an inclination angle (θtaper) from an angle (θout) of emitted light, two refractive indexes which are the refractive index $n_1$ of the light diffusing portion 3 including the inclined surface 3c and the refractive index $n_0$ of the periphery which is an emitting destination of light are included and the refractive index $n_2$ of the base material 2 is not included.

[Formula 1]

$$\theta_{taper} = 90° - \left[\frac{\sin^{-1}\left(\frac{n_0}{n_1 \sin\theta_{out}}\right) - \sin^{-1}\left(\frac{n_0}{n_1 \sin\theta_{in}}\right)}{2}\right] \quad (1)$$

Air normally exists around the light-regulating film 1, so that the refractive index $n_0$ of the periphery of the light-regulating film 1 is a refractive index of air, that is, $n_0=1$ is set. It is assumed that the refractive index m of the light diffusing portion 3 is 1.55, the refractive index $n_2$ of the base material 2 is 1.50, and the incident angle θin of the light L is 20°. When it is assumed that the emitting angle θout of transmitted light is obtained as 38° from measurement results of the light receiver 13, the inclination angle θtaper of the inclined surface 3c is calculated as 85° from the formula (1).

As described above, according to the inspection device 11 of the first embodiment, the inclination angle θtaper of the inclined surface 3c of the light diffusing portion 3 in the light-regulating film 1 can be calculated from measurement results of the light receiver 13. Accordingly, an inspector can inspect whether or not the light diffusing portion 3 which has a desired taper shape is produced. Thus, non-destructive inspection of the light-regulating film 1 is enabled and labor and time required for inspection of the light-regulating film 1 can be reduced. Further, damages of the light diffusing portion 3 associated with cutting of the light-regulating film 1 are not generated and a forming state of the light diffusing portion 3 can be reliably inspected.

The present inventors actually measured emitting angles θout of light when the incident angle θin of the light was changed and obtained a relation between the incident angle θin of light and the emitting angle θout of light on two kinds of light-regulating films 1 of which the inclined surfaces 3c of the light diffusing portions 3 have different inclination angles θtaper from each other. The measurement results are illustrated in [Table 1] and [Table 2]. [Table 1] shows measurement results of a case where the inclination angle θtaper is 85°, and [Table 2] shows measurement results of a case where the inclination angle θtaper is 80°. Here, the refractive indexes $n_0$, $n_1$, and $n_2$ are identical to the above-mentioned values. As an indicator representing directivity of the light source unit 12, the whole width of light emitted from the light source unit 12 is set to ±4°.

TABLE 1

| $\theta_{in}$ (°) | $\theta_{out}$ (°) |
|---|---|
| 0 | 16 |
| 5 | 21 |
| 10 | 26 |
| 15 | 31 |
| 20 | 37 |
| 25 | 42 |
| 30 | 48 |
| 35 | 54 |
| 40 | 61 |
| 45 | 69 |
| 50 | 89 |

TABLE 2

| $\theta_{in}$ (°) | $\theta_{out}$ (°) |
|---|---|
| 0 | 32 |
| 5 | 37 |
| 10 | 44 |
| 15 | 51 |
| 20 | 58 |
| 25 | 66 |
| 30 | 80 |

A refractive index of a general photosensitive material constituting the light diffusing portion 3 and a refractive index of a general base material 2 are in the range from 1.49 to 1.55. In this range of the refractive index, variation of calculated emitting angles θout was ±0.4°. Thus, the inclination angle θtaper of the inclined surface 3c could be obtained with sufficiently-high accuracy.

Second Embodiment

A second embodiment of the present invention is described below with reference to FIG. 5 and FIG. 6.

The basic configuration of an inspection device of the second embodiment is similar to that of the first embodiment but an operation of a light receiver is different from that of the first embodiment.

Figure 5:
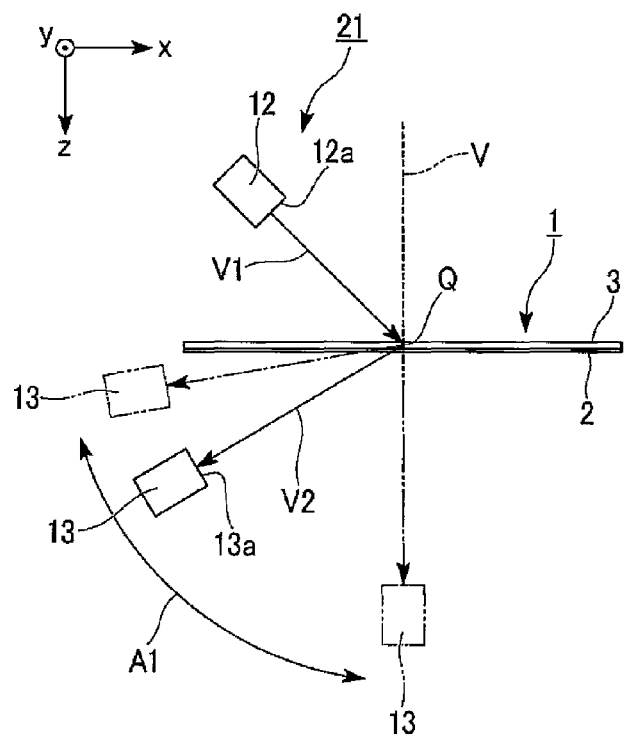
FIG. 5 is a lateral view illustrating an inspection device according to a second embodiment.
Figure 6:
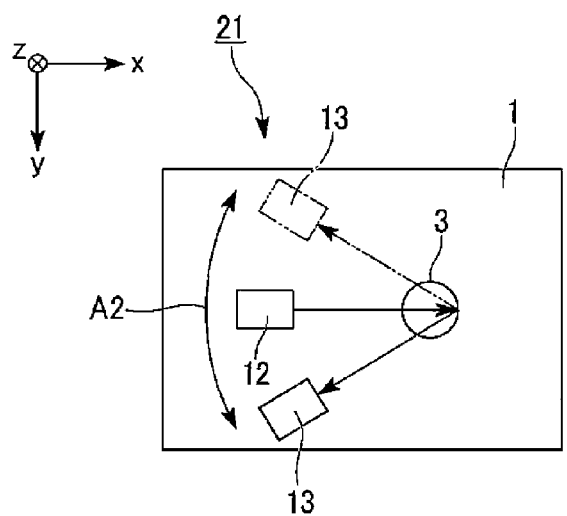
FIG. 6 is a plan view illustrating the inspection device.

In FIG. 5 and FIG. 6, constituent elements common to those in the drawings which are used in the first embodiment are given identical reference characters and descriptions thereof are omitted.

In the inspection device of the first embodiment, the light receiver is configured to move in the polar angle direction within a virtual plain surface which includes the normal line of the light emitting surface of the light source unit and the normal line of the light incident surface of the light receiver. On the other hand, in an inspection device 21 of the second embodiment as well, the light receiver 13 is configured to move in the polar angle direction illustrated by an arrow A1 within a virtual plain surface P which includes the normal line V1 of the light emitting surface 12a of the light source unit 12 and the normal line V2 of the light incident surface 13a of the light receiver 13 and is orthogonal to the principal surface of the light-regulating film 1, as illustrated in FIG. 5.

Further, as illustrated in FIG. 6, the light receiver 13 is configured to move in an azimuth angle direction illustrated by an arrow A2 within a virtual plain surface which is viewed from the normal line direction of the principal surface (a direction orthogonal to the principal surface) of the light-regulating film 1 in a given polar angle. That is, in the second embodiment, the normal line V1 of the light emitting surface 12a of the light source unit 12 and the normal line V2 of the light incident surface 13a of the light receiver 13 are not always positioned within the virtual plain surface P which is orthogonal to the principal surface of the light-regulating film 1 but the twisted positional relation is sometimes generated. When the light receiver 13 is moved in the azimuth angle direction, the light receiver 13 can acquire intensity distribution of reflection light with respect to the azimuth angle direction.

In the inspection device 21 of the second embodiment as well, the inclination angle θtaper of the inclined surface 3c of the light diffusing portion 3 in the light-regulating film 1 can be calculated from measurement results of the light receiver 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion 3 can be reliably inspected.

Further, according to the inspection device 21 of the second embodiment, reflection intensity distribution in the azimuth angle direction is acquired by moving the light receiver 13 in the azimuth angle direction. Accordingly, a plain surface shape of the light diffusing portion 3 can be grasped. For example, in a case where an intensity distribution curve in the azimuth angle direction is symmetric centering on the peak intensity when the light diffusing portion 3 which has a circular plain surface shape is inspected, it can be inferred that a curvature of a circle which is the plain surface shape of the light diffusing portion 3 is constant around a measurement point. In contrast, if the intensity distribution curve in the azimuth angle direction is asymmetric centering on the peak intensity, it can be inferred that a curvature of the circle which is the plain surface shape of the light diffusing portion 3 varies on the both sides of the measurement point.

Further, in a case where an asymmetric light diffusing portion 3 in which the inclination angle θtaper of the inclined surface 3c varies depending on the azimuth angle direction is inspected, if the light source unit 12 and the light receiver 13 are moved to the azimuth angle direction in a manner to be linked with each other, the inclination angle θtaper in a desired azimuth angle direction can be calculated.

Third Embodiment

A third embodiment of the present invention is described below with reference to FIG. 7 and FIG. 8.

The basic configuration of an inspection device of the third embodiment is similar to that of the first embodiment but an operation of a light receiver is different from that of the first embodiment.

Figure 7:
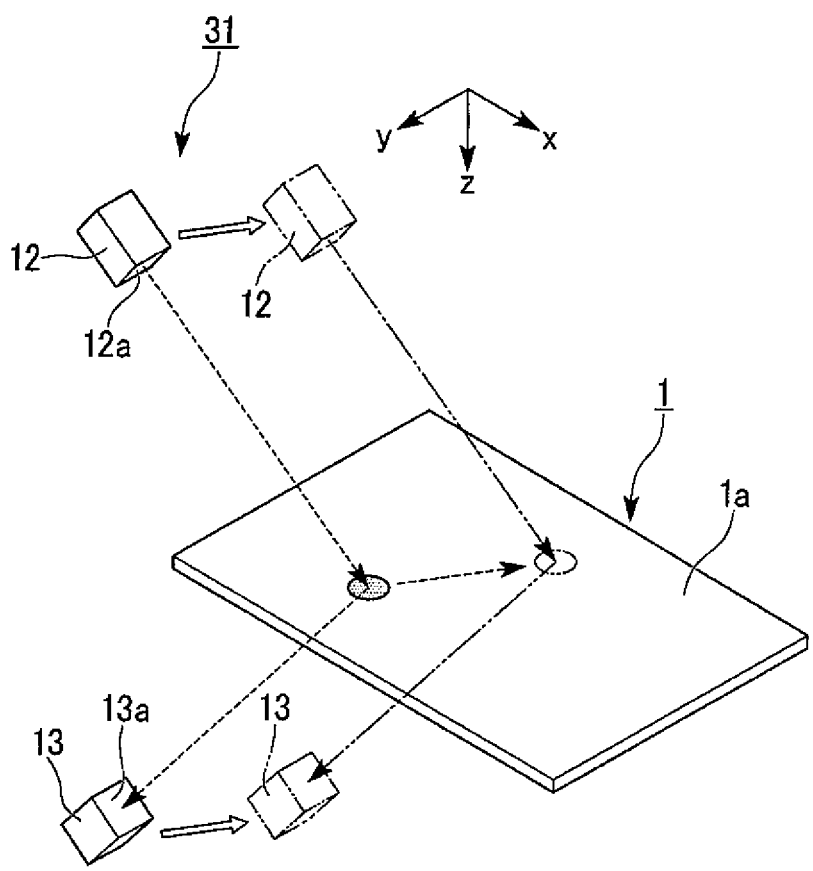
FIG. 7 is a perspective view illustrating an inspection device according to a third embodiment.
Figure 8:
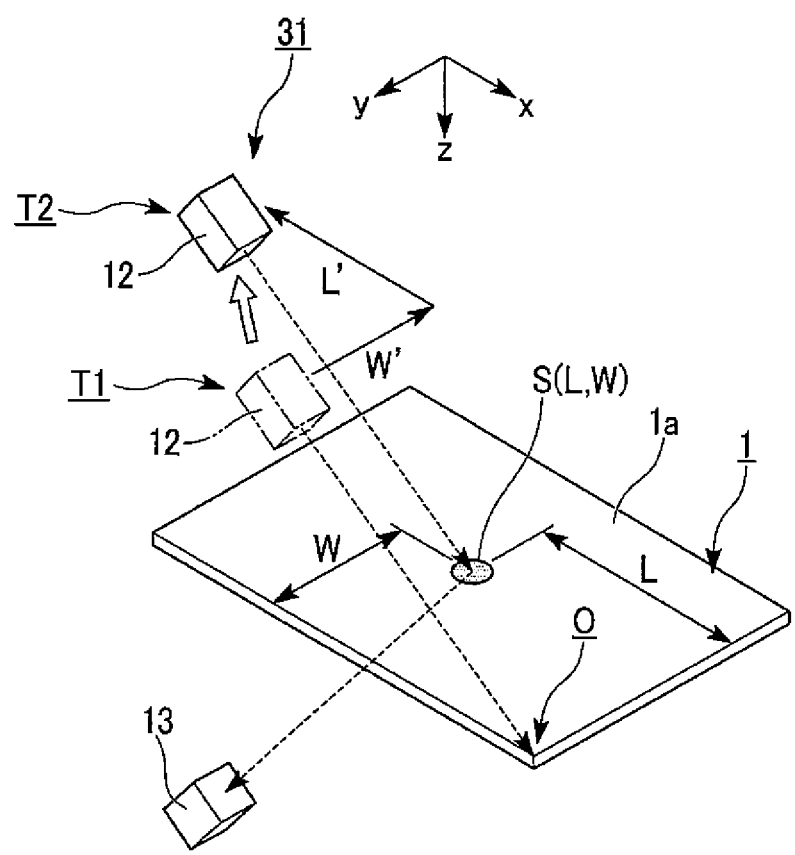
FIG. 8 is a perspective view for explaining a method for acquiring positional information by the inspection device.

In FIG. 7 and FIG. 8, constituent elements common to those in the drawings which are used in the first embodiment are given identical reference characters and descriptions thereof are omitted.

In an inspection device 31 of the third embodiment, the light source unit 12 is configured to be capable of moving in two directions (an x-axis direction, a y-axis direction) which are orthogonal to each other in a virtual plain surface which is parallel to the principal surface 1a of the light-regulating film 1, in an upper space of the light-regulating film 1, as illustrated in FIG. 7. The light receiver 13 is configured to be capable of moving in two directions (the x-axis direction, the y-axis direction) which are orthogonal to each other in a virtual plain surface which is parallel to the principal surface 1a of the light-regulating film 1, in a lower space of the light-regulating film 1. The light source unit 12 and the light receiver 13 move in a linked manner by the control of a control unit (not illustrated). The light source unit 12 and the light receiver 13 are capable of moving in the polar angle direction as is the case with the first embodiment. Here, in the following drawings, the light-regulating film 1 is simplified to be drawn like one plate for the sake of easy viewing of the drawings.

In the inspection device 31 of the third embodiment as well, the inclination angle θtaper of the inclined surface of the light diffusing portion in the light-regulating film 1 can be calculated from measurement results of the light receiver 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion can be reliably inspected.

The inspection device 11 of the first embodiment basically inspects one measurement point in a surface of the light-regulating film 1. However, if a position of the light-regulating film 1 with respect to the light source unit 12 and the light receiver 13 is changed in each case, even the inspection device 11 of the first embodiment can inspect a plurality of measurement points. On the other hand, the inspection device 31 of the third embodiment is capable of inspecting a plurality of measurement points without changing the position of the light-regulating film 1 by appropriately moving the light source unit 12 and the light receiver 13 in both of the x-axis direction and the y-axis direction.

If a light diffusing portion is not formed as the original design at any measurement point, in other words, if there is a defective part of a light diffusing portion, in inspection of a plurality of measurement points, the inspection device 31 of the third embodiment is capable of acquiring positional information of the defective part.

Specifically, as illustrated in FIG. 8, for example, one corner portion of the light-regulating film 1 is set as an origin O of a coordinate representing a position of the light-regulating film 1 and a position T1 of the light source unit 12 when the origin O is irradiated with light is set as a reference position of the light source unit 12. When a moving amount in the y-axis direction is denoted as W' and a moving amount in the x-axis direction is denoted as L' as a moving amount of the light source unit 12 from the reference position T1 of the light source unit 12 to a current position T2, a coordinate (L,W) of an irradiation position S of light emitted from the light source unit 12 on the current position T2 is expressed as L=L',W=W'. Accordingly, the control unit can obtain a defective part of a light diffusing portion as a coordinate based on the moving amount of the light source unit 12 from the reference position T1 of the light source unit 12 to the current position T2 and store the coordinate. The control unit corresponds to a positional information acquisition means in Claims.

Fourth Embodiment

A fourth embodiment of the present invention is described below with reference to FIG. 9.

The basic configuration of an inspection device of the fourth embodiment is similar to that of the first embodiment but the number of light receivers is different from that of the first embodiment.

Figure 9:
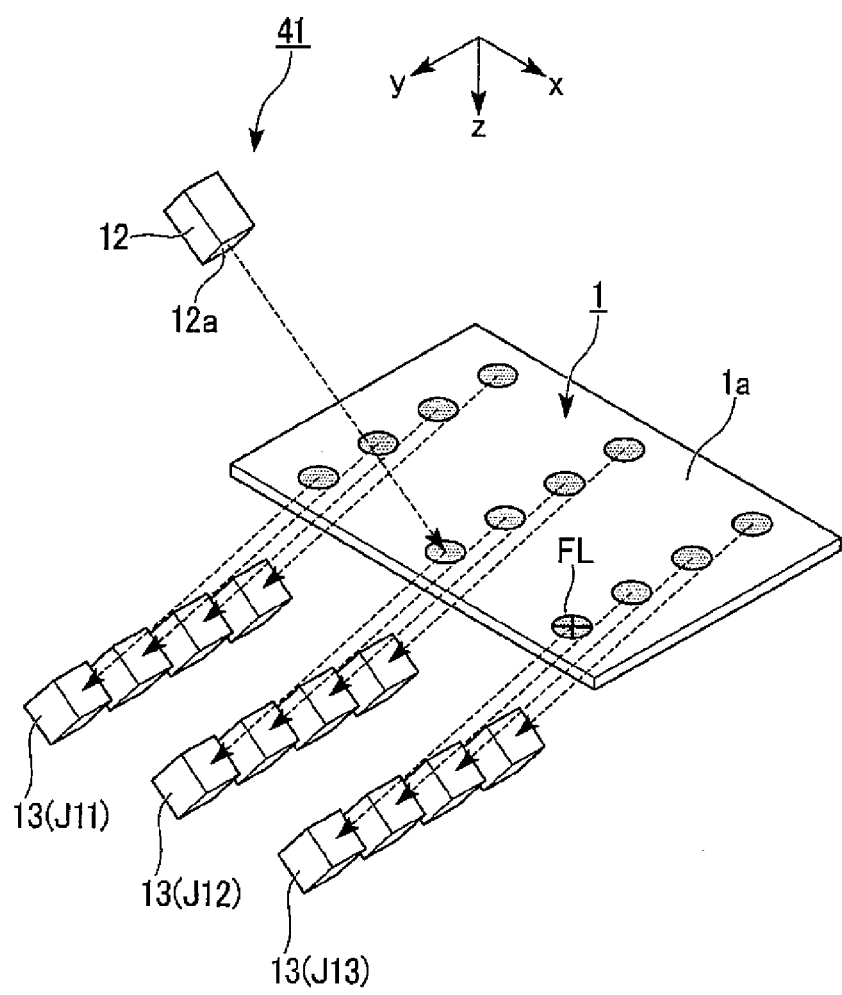
FIG. 9 is a perspective view illustrating an inspection device according to a fourth embodiment.

In FIG. 9, constituent elements common to those in the drawings which are used in the first embodiment are given identical reference characters and descriptions thereof are omitted.

As illustrated in FIG. 9, an inspection device 41 of the fourth embodiment is provided with a plurality of light receivers 13. A plurality of light receivers 13 are arranged in a matrix with mutual intervals in each of the x-axis direction and the y-axis direction. As is the case with the first embodiment, each of a plurality of light receivers 13 is capable of independently moving in the polar angle direction. Further, each of a plurality of light receivers 13 may be capable of independently moving in the azimuth angle direction. However, a plurality of light receivers 13 do not move in a virtual plain surface which is parallel to the principal surface 1a of the light-regulating film 1. On the other hand, the light source unit 12 is configured to be capable of moving in the x-axis direction and the y-axis direction in the virtual plain surface which is parallel to the principal surface 1a of the light-regulating film 1. Accordingly, the light source unit 12 is capable of moving to a plurality of positions, which correspond to respective light receivers 13, on the light-regulating film 1.

In the inspection device 41 of the fourth embodiment as well, the inclination angle θtaper of the inclined surface of the light diffusing portion of the light-regulating film 1 can be calculated from measurement results of the light receivers 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion can be reliably inspected.

The inspection device 41 of the fourth embodiment is capable of inspecting a plurality of measurement points without moving the light-regulating film 1 as is the case with the inspection device of the third embodiment. The inspection device 41 of the fourth embodiment is also capable of inspecting a plurality of measurement points, and if there is a defective part of the light diffusing portion, the inspection device 41 is capable of acquiring positional information of the defective part.

Specifically, identification numbers for identifying the light receivers 13 are provided to a plurality of light receivers 13 as J11, J12, J13, . . . , J31, J32, and J33, for example. The control unit stores an identification number of a light receiver 13 which has detected a defective part among the plurality of light receivers 13 so as to be able to specify a position, which corresponds to the light receiver 13, on the light-regulating film 1 as the defective part. If a light receiver 13 provided with the identification number J13 has detected a defective part FL, for example, a position, which corresponds to the light receiver 13 provided with the identification number J13, on the light-regulating film 1 is specified as a defective part. The control unit corresponds to a positional information acquisition means in Claims.

Fifth Embodiment

A fifth embodiment of the present invention is described below with reference to FIG. 10.

The basic configuration of an inspection device of the fifth embodiment is similar to that of the first embodiment but the configuration of a light source unit is different from that of the first embodiment.

Figure 10:
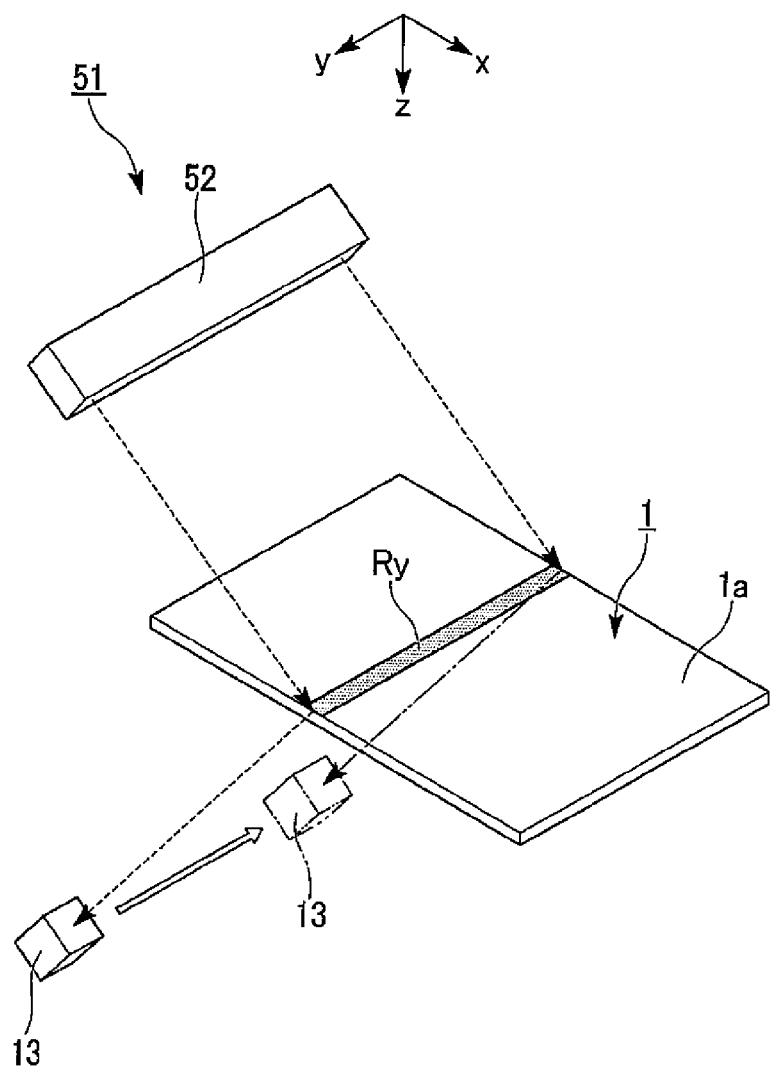
FIG. 10 is a perspective view illustrating an inspection device according to a fifth embodiment.

In FIG. 10, constituent elements common to those in the drawings which are used in the first embodiment are given identical reference characters and descriptions thereof are omitted.

As illustrated in FIG. 10, an inspection device 51 of the fifth embodiment is provided with a light source unit 52 which is composed of a linear light source. The light source unit 52 emits linear light which extends in the y-axis direction. The light source unit 52 emits light which is irradiated to a predetermined linear region Ry on the light-regulating film 1. The light receiver 13 is same as that of the first embodiment. The light receiver 13 moves in parallel with the y-axis direction in a virtual plain surface which is parallel to the principal surface 1a of the light-regulating film 1. The light receiver 13 moves in the polar angle direction as is the case with the first embodiment. As is the case with the second embodiment, the light receiver 13 may be capable of moving in the azimuth angle direction. Further, the light source unit 52 and the light receiver 13 may move in parallel with the x-axis direction in the virtual plain surface which is parallel to the principal surface 1a of the light-regulating film 1 in a mutually-linked manner. Instead of the light receiver 13, a linear light receiver which corresponds to the light source unit 52 may be used.

In the inspection device 51 of the fifth embodiment as well, the inclination angle θtaper of the inclined surface of the light diffusing portion of the light-regulating film 1 can be calculated from measurement results of the light receiver 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion can be reliably inspected.

The inspection device 51 of the fifth embodiment is capable of inspecting a plurality of measurement points along the y-axis direction at a specific position in the x-axis direction, without moving the light-regulating film 1. Further, if such configuration is employed that the light source unit 52 and the light receiver 13 move in parallel in the x-axis direction as well in a linked manner, a plurality of measurement points can be inspected in the whole surface of the light-regulating film 1. The inspection device 51 of the fifth embodiment may also be configured such that the inspection device 51 inspects a plurality of measurement points and if there is a defective part of the light diffusing portion, the inspection device 51 acquires a positional coordinate of the defective part, by a method similar to that of the third embodiment.

Sixth Embodiment

A sixth embodiment of the present invention is described below with reference to FIG. 11.

The basic configuration of an inspection device of the sixth embodiment is similar to that of the first embodiment but the configuration of a light source unit is different from that of the first embodiment.

Figure 11:
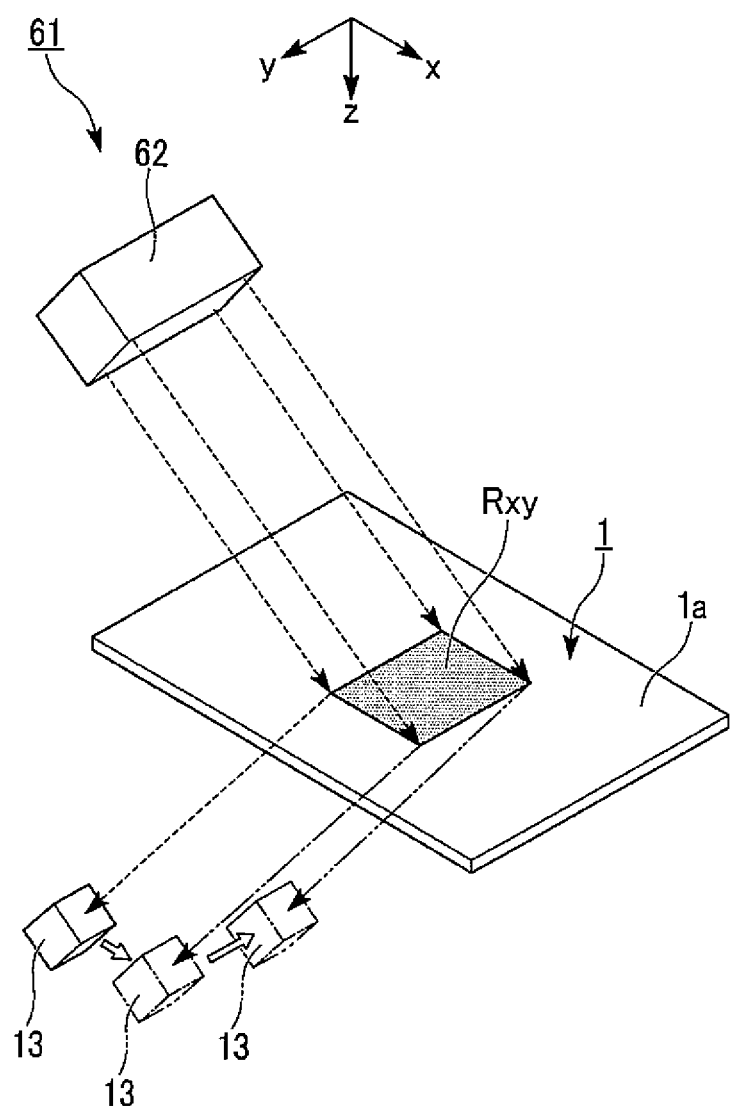
FIG. 11 is a perspective view illustrating an inspection device according to a sixth embodiment.

In FIG. 11, constituent elements common to those in the drawings which are used in the first embodiment are given identical reference characters and descriptions thereof are omitted.

As illustrated in FIG. 11, an inspection device 61 of the sixth embodiment is provided with a light source unit 62 which is composed of a planar light source. The light source unit 62 emits light which is irradiated to a predetermined rectangular region Rxy on the light-regulating film 1. An irradiation region of light does not necessarily have a rectangular shape but may have a circular shape, for example. The light receiver 13 moves in parallel with both of the x-axis direction and the y-axis direction in a virtual plain surface which is parallel to the principal surface 1a of the light-regulating film 1. The light receiver 13 is capable of moving in the polar angle direction as is the case with the first embodiment. The light receiver 13 may be capable of moving in the azimuth angle direction as is the case with the second embodiment. Further, the light source unit 62 and the light receiver 13 may move in parallel with the x-axis direction and the y-axis direction in the virtual plain surface which is parallel to the principal surface 1a of the light-regulating film 1 in a mutually-linked manner.

In the inspection device 61 of the sixth embodiment as well, the inclination angle θtaper of the inclined surface of the light diffusing portion of the light-regulating film 1 can be calculated from measurement results of the light receiver 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion can be reliably inspected.

The inspection device 61 of the sixth embodiment is capable of inspecting a plurality of measurement points on the light-regulating film 1 without moving the light-regulating film 1. The inspection device 61 of the sixth embodiment may also be configured such that the inspection device 61 inspects a plurality of measurement points and if there is a defective part of the light diffusing portion, the inspection device 61 acquires a positional coordinate of the defective part, by a method similar to that of the third embodiment.

Seventh Embodiment

A seventh embodiment of the present invention is described below with reference to FIG. 12 and FIG. 13.

The basic configuration of an inspection device of the seventh embodiment is similar to that of the first embodiment but a positional relation between a light source unit and a light receiver is different from that of the first embodiment.

Figure 12:
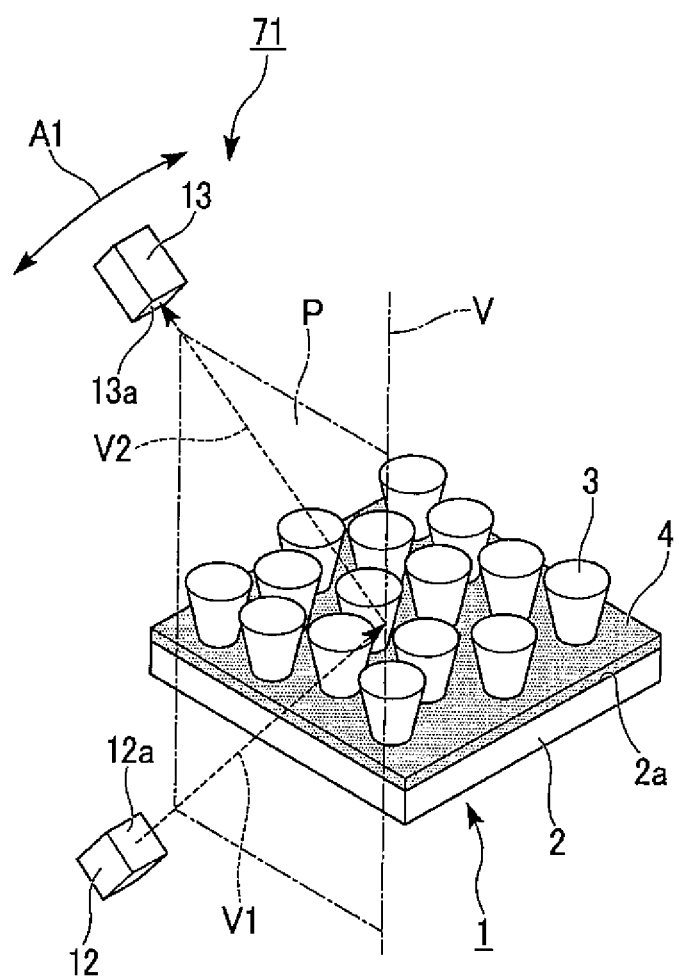
FIG. 12 is a perspective view illustrating an inspection device according to a seventh embodiment.
Figure 13:
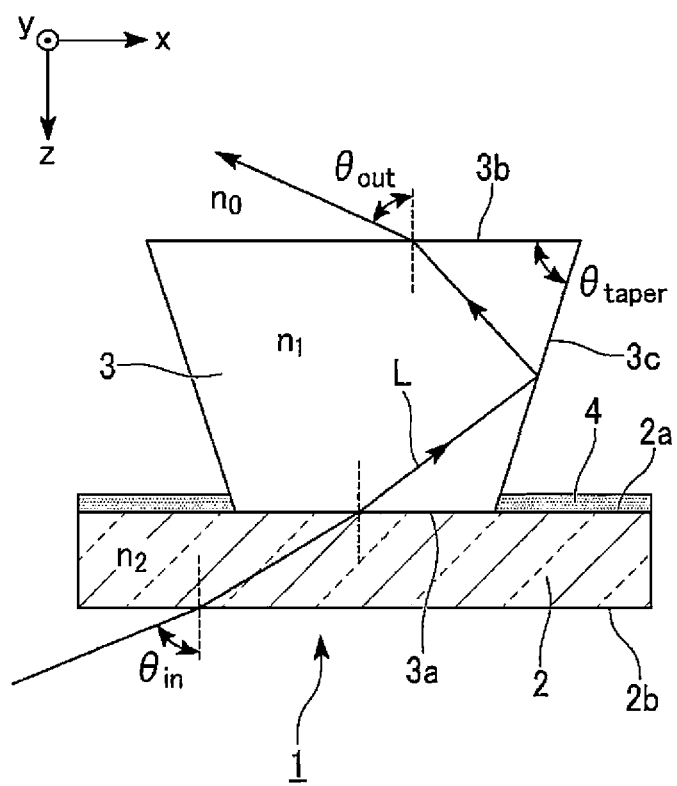
FIG. 13 is a sectional view illustrating a state of reflection in the light-regulating film.

In FIG. 12 and FIG. 13, constituent elements common to those in the drawings which are used in the first embodiment are given identical reference characters and descriptions thereof are omitted.

As illustrated in FIG. 12, in an inspection device 71 of the seventh embodiment, the light source unit 12 is disposed on the base material 2 side of the light-regulating film 1 and radiates light toward the light-regulating film 1. The light receiver 13 is disposed on the light diffusing portion 3 side of the light-regulating film 1 and measures the intensity of transmitted light which is emitted from the light source unit 12 and is transmitted through the light-regulating film 1. That is, in the inspection device 71 of the seventh embodiment, a positional relation between the light source unit 12 and the light receiver 13 is inverted with respect to that of the first embodiment. Other configurations are same as those of the first embodiment.

In the seventh embodiment, as illustrated in FIG. 13, an incident angle of light L which is incident on the base material 2 from the light source unit 12 is θin and an emitting angle of light which is emitted from the light incident end surface 3b of the light diffusing portion 3 is θout. Here, the light incident end surface 3b referred here represents a surface on which light is incident in the use of the light-regulating film 1. Accordingly, in a case of the inspection device 71 of the seventh embodiment, a direction in which the light L travels in the light-regulating film 1 is opposite to an actual use form of the light-regulating film 1 and is opposite to the inspection device of the first embodiment. When the inclination angle θtaper of the inclined surface 3c of the light diffusing portion 3 is calculated, the following formula (2) can be used. As is the case with the formula (1), a medium having the refractive index $n_2$, that is, the light-regulating film 1 is a parallel plain plate, so that light is merely transmitted through the light-regulating film 1 and the light-regulating film 1 does not affect an angle of emitted light. Accordingly, in the formula (2) for obtaining an inclination angle (θtaper) from an angle (θout) of emitted light, two refractive indexes which are the refractive index $n_1$ of the light diffusing portion 3 including the inclined surface 3c and the refractive index $n_0$ of the periphery which is an emitting destination of light are included and the refractive index $n_2$ of the base material 2 is not included.

[Formula 2]

$$\theta_{taper} = 90° - \left[\frac{\sin^{-1}\left(\frac{n_0}{n_1}\sin\theta_{in}\right) - \sin^{-1}\left(\frac{n_0}{n_1}\sin\theta_{out}\right)}{2}\right] \quad (2)$$

In the inspection device 71 of the seventh embodiment as well, the inclination angle θtaper of the inclined surface of the light diffusing portion of the light-regulating film 1 can be calculated from measurement results of the light receiver 13 by a procedure similar to that of the inspection device of the first embodiment. Accordingly, such advantageous effects, which are same as those of the first embodiment, can be obtained that non-destructive inspection of the light-regulating film 1 is enabled, labor and time required for inspection of the light-regulating film 1 can be reduced, and a forming state of the light diffusing portion can be reliably inspected.

Figure 18:
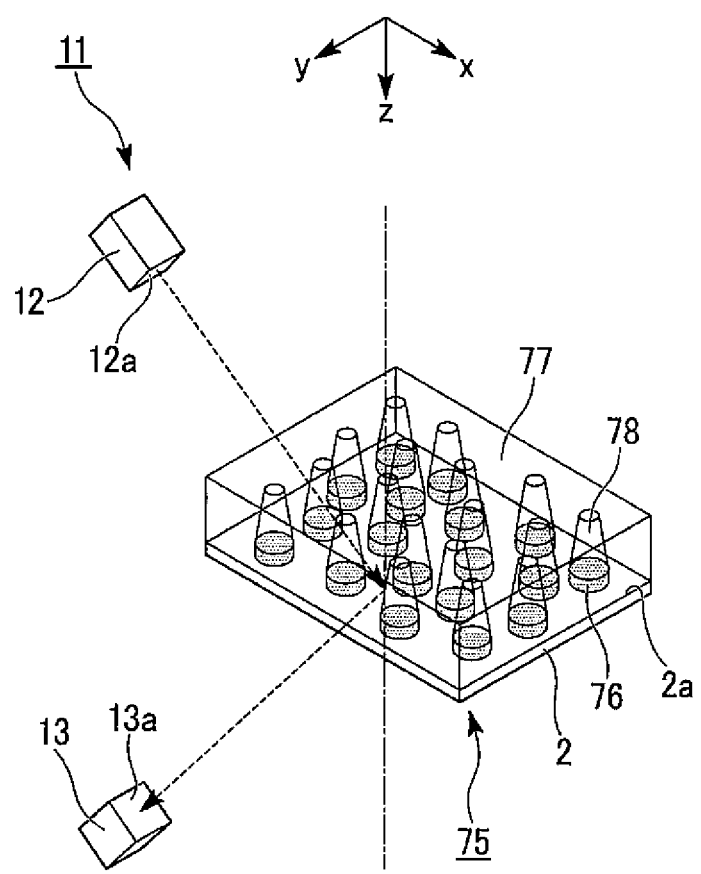
FIG. 18 is a perspective view illustrating a modification example of a light-regulating film which is an inspection object.

A light-regulating film 75 illustrated in FIG. 18 includes the base material 2, a plurality of light shielding layers 76 which are formed on the first surface 2a of the base material 2, and a light diffusing portion 77 which is formed in a region other than forming regions of a plurality of light shielding layers 76. Spaces 78 having a circular truncated cone shape are formed in the forming regions of the light shielding layers 76 and air exists in the spaces 78. The light-regulating film 75 includes the light diffusing portion 77 portion of which other than the spaces 78 are continued in a wall shape.

Even in a case where this light-regulating film 75 is an inspection object, inspection can be performed in a similar manner by using the inspection devices of the first to seventh embodiments.

Eighth Embodiment

An eighth embodiment of the present invention is described below with reference to FIG. 14 to FIG. 16.

In the eighth embodiment, an example of a production device for a light-regulating film including an inspection device similar to that of the first to seventh embodiments is cited. In the following description, the "production device for a light-regulating film" is merely referred to as a "production device".

Figure 14:
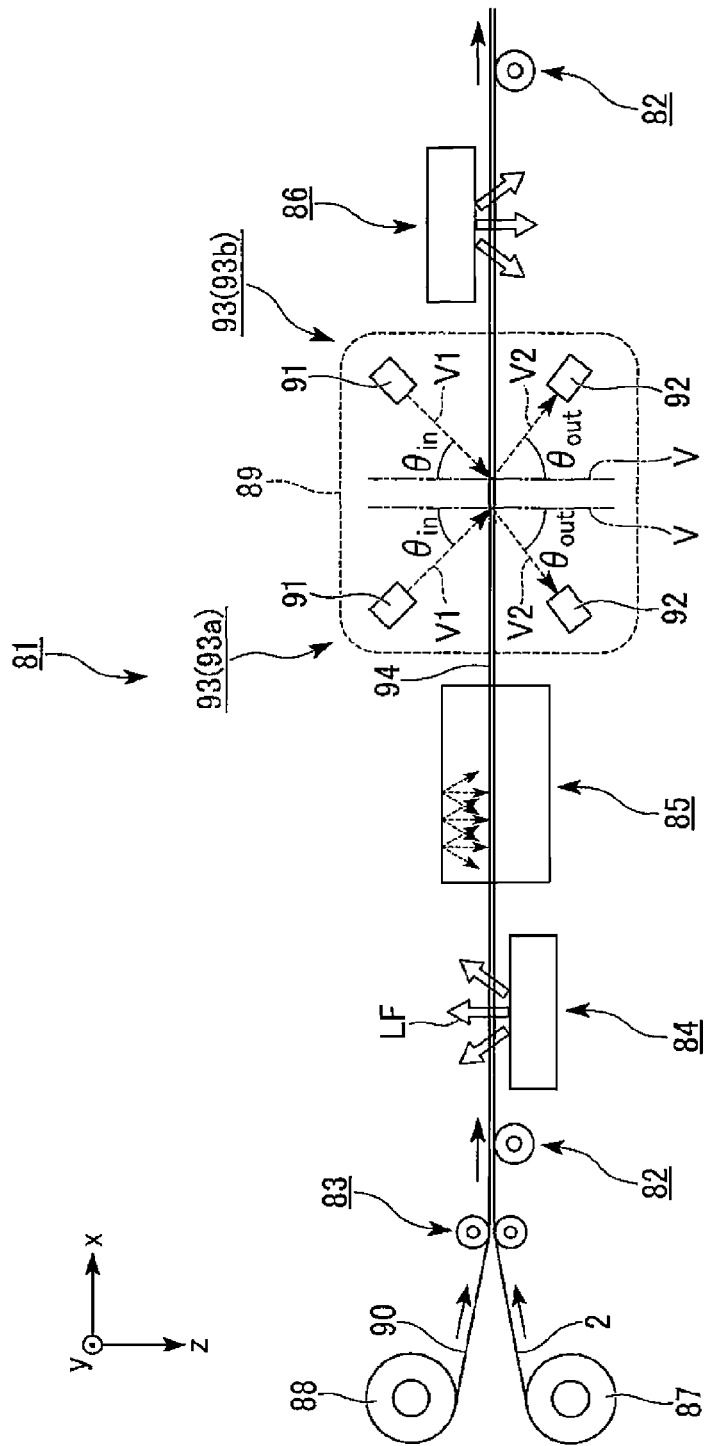
FIG. 14 is a lateral view illustrating a production device for a light-regulating film according to an eighth embodiment.

FIG. 14 is a schematic configuration diagram illustrating a production device of the eighth embodiment.

Figure 15:
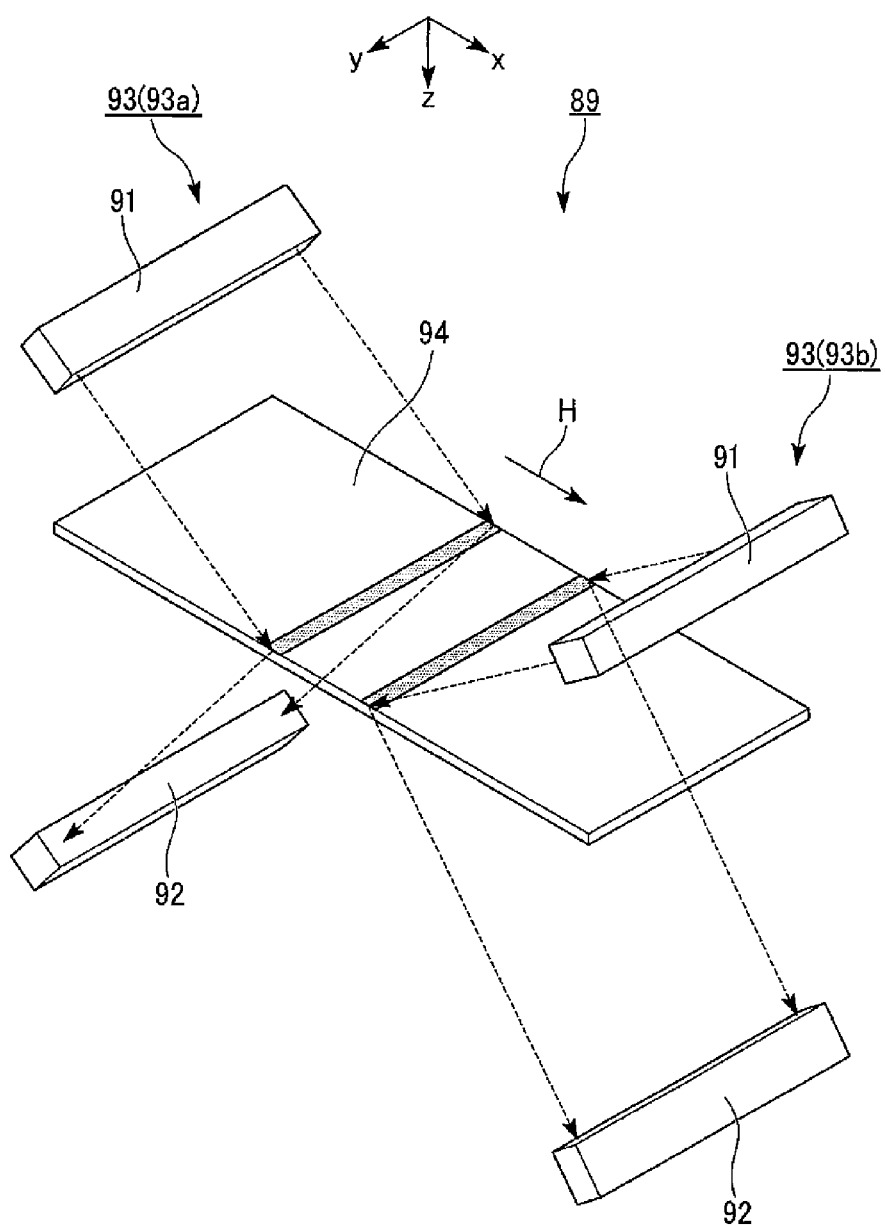
FIG. 15 is a perspective view illustrating the inspection device which is incorporated into the production device.

In FIG. 14 to FIG. 16, constituent elements common to those in the drawings which are used in the first embodiment are given identical reference characters and descriptions thereof are omitted.

A production device 81 of the eighth embodiment is a production device which products a long light-regulating film in a continuously conveying manner and then cuts the light-regulating film in accordance with the size of each display device.

As illustrated in FIG. 14, the production device 81 is provided with a plurality of processing devices and a conveying device 82 which conveys a light-regulating film in the middle of production among a plurality of processing devices. A plurality of processing devices include a laminate device 83, a back surface exposure device 84, a developing/water-washing/drying device 85, and a curing-exposure device 86. As the conveying device 82, a general conveying device such as a roller conveyer is used. The production device 81 further includes a base material supply roller 87, a photosensitive resin film supply roller 88, and the like.

An inspection device 89 is disposed in the middle of a conveying path of the light-regulating film 1 in the conveying device 82. Specifically, the inspection device 89 is disposed between the developing/water-washing/drying device 85 and the curing-exposure device 86 in this example.

A flow of the whole processing of the production device 81 is described. Here, an example for producing the light-regulating film 75 illustrated in FIG. 18 is described.

The base material 2 on which a plurality of light shielding layers are formed is supplied from the base material supply roller 87. Meanwhile, a photosensitive resin film 90 which is made of a negative-type photosensitive resin and which will be a light diffusing portion later is supplied from the photosensitive resin film supply roller 88. Then, the base material 2 and the photosensitive resin film 90 are bonded with each other by the laminate device 83.

Then, the back surface exposure device 84 radiates diffused light LF with respect to the photosensitive resin film 90 from the base material 2 side to expose the photosensitive resin film 90 to light through the base material 2. At this time, the light shielding layers are formed on the base material 2, so that the light shielding layers serve as masks. Accordingly, light is not radiated to portions of circular truncated cone shapes bottom surfaces of which are the light shielding layers, in the photosensitive resin film 90.

Then, the developing/water-washing/drying device 85 performs developing processing of photosensitive resin so as to form a light diffusing portion which has spaces in portions of circular truncated cone shapes bottom surfaces of which are the light shielding layers. After that, water-washing processing for washing a developing solution and drying processing are performed.

Then, the inspection device 89 performs inspection of a light-regulating film on which the light diffusing portion has been formed. Details of the inspection device 89 will be described later.

Then, the curing-exposure device 86 performs curing-exposure for reliably curing the light diffusing portion with respect to the light-regulating film after completion of the inspection.

After that, through operations of reflection protecting processing of a back surface of the base material 2 which is on the visual observation side, cutting, and the like, a light-regulating film is completed.

Here, in a case where a light-regulating film is used for a liquid crystal display, an operation for preliminarily bonding a polarization plate on the light-regulating film may be added before the light-regulating film is bonded on a liquid crystal display.

As illustrated in FIG. 15, the inspection device 89 is provided with two inspection units 93 each of which is composed of a pair of a light source unit 91 and a light receiver 92. In the following description, a conveying direction H of a light-regulating film 94 and a direction which is orthogonal to the conveying direction H of the light-regulating film 94 are sometimes referred to as a length direction of the light-regulating film 94 and a width direction of the light-regulating film 94 respectively. The light source unit 91 is composed of a linear light source which has a dimension approximately accorded with a dimension of the light-regulating film 94 in the width direction. In a similar manner, the light receiver 92 has a light receiving surface which has a dimension approximately accorded with the dimension of the light-regulating film 94 in the width direction.

The light source unit 91 is disposed in an upper space of the light-regulating film 94. The light receiver 92 is disposed in a lower space of the light-regulating film 94. The light source unit 91 is disposed so that the incident angle θin which is made by an optical axis V1 of light incident on the light-regulating film 94 and the normal line direction V of the light-regulating film 94 is 20°. In a case where the inclination angle θtaper of the inclined surface of the light diffusing portion of the light-regulating film 94 is 85°, the light receiver 92 is disposed so that the emitting angle θout which is made by an optical axis V2 of light emitted from the light-regulating film 94 and the normal line direction V of the light-regulating film 94 is 38°.

The light receiver 92 is disposed on a position at which the intensity of transmitted light reaches the peak intensity when the inclination angle θtaper of the inclined surface of the light diffusing portion is 85°. The inspection device 89 of the present embodiment is not used for measuring the inclination angle θtaper of the inclined surface of the light diffusing portion. The inspection device 89 of the present embodiment is basically used for performing determination of whether or not the light diffusing portion of the light-regulating film 94 has a desired inclination angle θtaper, that is, determination of nondefective/defective of the light diffusing portion in a manner to be incorporated into the production device 81. Accordingly, the light receiver 92 need not move in the polar angle direction differently from the inspection device of the first embodiment. However, the light receiver may be configured to move in the polar angle direction so as to be able to measure the inclination angle θtaper of the inclined surface of the light diffusing portion.

In a first inspection unit 93a, the light source unit 91 irradiates linear light at a tilt from the upper stream side to the lower stream side of the conveying direction H of the light-regulating film 94. The light receiver 92 receives the light which reflects at the light diffusing portion of the light-regulating film 94 and travels at a tilt from the lower stream side to the upper stream side of the conveying direction H. In a second inspection unit 93b, the light source unit 91 irradiates linear light at a tilt from the lower stream side to the upper stream side of the conveying direction H of the light-regulating film 94. The light receiver 92 receives the light which reflects at the light diffusing portion of the light-regulating film 94 and travels at a tilt from the upper stream side to the lower stream side of the conveying direction H. The inspection device 89 is provided with such two inspection units 93a and 93b, so that the inclined surface, which is viewed from two directions (a positive side of the x-axis direction, a negative side of the x-axis direction), of the light diffusing portion can be inspected.

Here, there is a case where portion of light which is emitted from the light source unit 91 of one inspection unit 93 travels straight and passes through the light-regulating film 94 without being reflected at the light diffusing portion of the light-regulating film 94. If such light is incident on the light receiver 92 of the other inspection unit 93, accurate inspection may not be able to be performed. To avoid such defect, it is preferable that the first inspection unit 93a and the second inspection unit 93b be disposed with a sufficient interval with which light which is emitted from the light source unit 91 of one inspection unit 93 and travels straight through the light-regulating film 94 is not incident on the light receiver 92 of the other inspection unit 93.

In either inspection unit 93, light is constantly emitted from the light source unit 91 and transmitted light from the light-regulating film 94 is constantly detected at the light receiver 92.

Figures 16A, 16B:
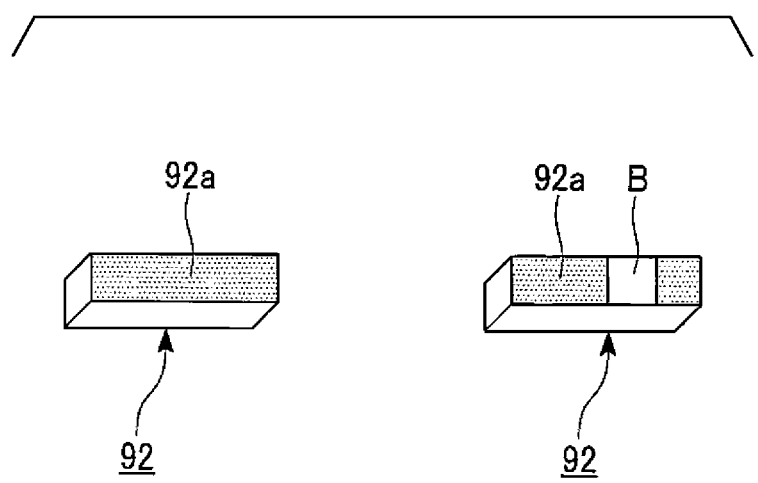
FIGS. 16 (A) and (B) are perspective views illustrating a state of a light receiving surface of a light receiver.

FIGS. 16 (A) and (B) illustrate a light receiving surface 92a of the light receiver 92 and a part on which light is actually detected is illustrated by hatching. In a case where the incident angle θin of light from the light source unit 91 is 20°, light the emitting angle θout of which is 38° is supposed to be detected as the peak intensity by the light receiver 92 if the inclination angle θtaper of the inclined surface of the light diffusing portion is formed to 85° as designed. Accordingly, if light diffusing portions in the whole region in the width direction of the light-regulating film 94 are non-defective products, light is detected in the whole region of the light receiving surface 92a as illustrated in FIG. 16(A).

On the other hand, if a light diffusing portion in a part of the region in the width direction of the light-regulating film 94 is a defective product, a dark portion B in which light is not detected is generated in a part of the light receiving surface 92a, as illustrated in FIG. 16(B). In a case where the dark portion B is detected, a distance from a reference position of the light-regulating film 94 (a start end of the light-regulating film 94, for example) to a current detecting point is taken as the x-axis coordinate and a distance from one end in the width direction of the light-regulating film 94 to the defective part is taken as the y-axis coordinate. Thus, positional information of a defective part can be acquired.

The production device 81 of the present embodiment is provided with the inspection device 89 in a conveying path of the light-regulating film 94, so that the production device 81 is capable of continuously performing non-destructive inspection of the light diffusing portions. Accordingly, the production device 81 is capable of producing a light-regulating film having an excellent quality without stopping conveyance of the light-regulating film 94 in the middle or lowering productivity.

Ninth Embodiment

A ninth embodiment of the present invention is described below with reference to FIG. 17.

The basic configuration of a production device of the ninth embodiment is approximately same as the production device of the eighth embodiment but the configuration of an inspection device is different from that of the production device of the eighth embodiment.

FIG. 17 is a schematic configuration diagram illustrating an inspection device which is provided to the production device of the ninth embodiment.

In FIG. 17, constituent elements common to those in the drawings which are used in the eighth embodiment are given identical reference characters and descriptions thereof are omitted.

A production device of the ninth embodiment is a production device which performs processing of each operation with respect to each region which is obtained by dividing a long light-regulating film in the longitudinal direction while intermittently conveying the long light-regulating film and then cuts the light-regulating film in accordance with the size of each display device.

As illustrated in FIG. 17, an inspection device 99 is provided with two inspection units 102 each of which is composed of a light source unit 100 and a plurality of light receivers 101. The light source unit 100 is composed of a planar light source which has a dimension in the y-axis direction approximately accorded with a dimension of the light-regulating film 94 in the width direction. A radiation range R of light emitted from the light source unit 100 is equal to a range corresponding to one-step movement in intermittent conveyance of the light-regulating film 94. A plurality of light receivers 101 are arranged in a matrix within a range in which the light receivers 101 can receive transmitted light which is emitted from the above-mentioned radiation range R of the light-regulating film 94.

The light source unit 100 is disposed in the upper space of the light-regulating film 94. A plurality of light receivers 101 are disposed in the lower space of the light-regulating film 94. In a similar manner to the eighth embodiment, the light source unit 100 is disposed so that the incident angle θin made by the optical axis of light which is incident on the light-regulating film 94 and the normal line direction of the light-regulating film 94 is 20°. In a case where the inclination angle θtaper of the inclined surface of the light diffusing portion of the light-regulating film 94 is 85°, a plurality of light receivers 101 are disposed on positions on which the emitting angle θout made by the optical axis of light emitted from the light-regulating film 94 and the normal line direction of the light-regulating film 94 is 38°. The light receivers 101 are disposed on positions at which the intensity of transmitted light becomes the peak intensity when the inclination angle θtaper of the inclined surface of the light diffusing portion is 85°. The light receivers 101 may move in the polar angle direction or do not have to move in the polar angle direction.

In a first inspection unit 102a, the light source unit 100 radiates planar light at a tilt from an upper stream side to a lower stream side of the conveying direction H of the light-regulating film 94. A plurality of light receivers 101 receive the light which reflects at the light diffusing portion of the light-regulating film 94 and travels at a tilt from the lower stream side to the upper stream side of the conveying direction H. In a second inspection unit 102b, the light source unit 100 irradiates planar light at a tilt from the lower stream side to the upper stream side of the conveying direction H of the light-regulating film 94. A plurality of light receivers 101 receive the light which reflects at the light diffusing portion of the light-regulating film 94 and travels at a tilt from the upper stream side to the lower stream side of the conveying direction H. The inspection device 99 is provided with such two inspection units 102, so that the inclined surface, which is viewed from two directions (a positive side of the x-axis direction, a negative side of the x-axis direction), of the light diffusing portion can be inspected.

Here, it is preferable to dispose the first inspection unit 102a and the second inspection unit 102b with an interval larger than a distance of one-step movement so that in light emitted from the light source unit 100 of one inspection unit 102, light which travels straight and passes through the light-regulating film 94 is not incident on the light receiver 101 of the other inspection unit 102.

In the inspection device 99, light is constantly emitted from the light source unit 100 and transmitted light from the light-regulating film 94 is constantly detected at a plurality of light receivers 101. If a light diffusing portion in a part of a light irradiation region of the light-regulating film 94 is a defective product, the control unit sets the number of steps from a reference position of the light-regulating film 94 (a start end of the light-regulating film 94, for example) to a current position and an identification number of the light receiver 101 which has detected the defective part as positional information of the defective part.

In the production device of the present embodiment as well, such advantageous effect, which is same as that of the eighth embodiment, can be obtained that a light-regulating film having an excellent quality can be produced without lowering productivity.

The inspection devices of the eighth embodiment and the ninth embodiment may be configured such that the light receivers are moved in the polar angle direction so as to measure the inclination angle θtaper of the inclined surface of the light diffusing portion in a similar manner to the inspection device 11 of the first embodiment. In this case, the inspection device may be configured not only to determine nondefective/defective of the light diffusing portion but also to feed back measurement results of the inclination angle θtaper in the production device.

As an example, there is such configuration that a measurement result of the inclination angle θtaper is fed back to the back surface exposure device. There is such relation that as the exposure amount in back surface exposure is larger, the inclination angle θtaper of the inclined surface of the light diffusing portion is reduced, and as the exposure amount in back surface exposure is smaller, the inclination angle θtaper of the inclined surface of the light diffusing portion is increased. Accordingly, in a case where a measurement result of the inclination angle θtaper is larger than a target value of the inclination angle θtaper, the exposure amount of the back surface exposure device may be increased, while, in a case where a measurement result of the inclination angle θtaper is smaller than a target value of the inclination angle θtaper, the exposure amount of the back surface exposure device may be reduced. If the production device performs such feedback, determination of nondefective/defective of the light-regulating film can be performed and a yield of the light-regulating film can also be improved.

The example of the light-regulating film 1 which is illustrated in FIG. 1 and includes a plurality of light diffusing portions 3 which are formed on the first surface 2a of the base material 2 and the light shielding layer 4 which is formed in a region other than the forming region of a plurality of light diffusing portions 3 is cited as an inspection object of the first to ninth embodiments. However, in all of the embodiments, an inspection object is not limited to the light-regulating film 1 having the configuration illustrated in FIG. 1 but may be the light-regulating film illustrated in FIG. 18.

Here, the technical scope of the present invention is not limited to the above-described embodiments but various alterations can be made without deviating from the object of the present invention.

For example, one example in which the number of light source units is one has been provided in the inspection device of the above-described embodiments, but a plurality of light source units may be provided. Apart from that, as for the specific configurations of the inspection device and the production device for a light-regulating film, arbitrary alterations can be made other than the configurations illustrated in the above-described embodiments.

INDUSTRIAL APPLICABILITY

The present invention is applicable to inspection of a light-regulating film which can be used for various types of display devices such as a liquid crystal display device, an organic electroluminescence display device, and a plasma display.

REFERENCE SIGNS LIST

1, 75, 94 light-regulating film
2 base material
3, 77 light diffusing portion
4, 76 light shielding layer (light shielding portion)
11, 21, 31, 41, 51, 61, 71, 89, 99 inspection device
12, 52, 62, 91, 100 light source unit
13, 92, 101 light receiver (light measurement means)
81 production device
82 conveying device
83 laminate device (processing device)
84 back surface exposure device (processing device)

85 developing/water-washing/drying device (processing device)
86 curing-exposure device (processing device)

The invention claimed is:

1. An inspection device for a light-regulating film, comprising:
a light source that is on either one of a base material side and a light diffusing portion side and radiates light toward the light-regulating film, the light-regulating film including:
the base material having a light transmitting property,
the light diffusing portion on a first surface of the base material, the light diffusing portion including a light emitting end surface on the base material side, a light incident end surface on a side opposite to the base material and has an area larger than an area of the light emitting end surface, and an inclined surface inclined with respect to the light emitting end surface, wherein a height from the light incident end surface to the light emitting end surface of the light diffusing portion is larger than a layer thickness of a light shielding portion, and
the light shielding portion being provided in a region other than a region defining the light diffusing portion in the first surface,
a light receiver on either the base material side or the light diffusing portion side not irradiated by the light source, the light receiver measuring an intensity of transmitted light that is emitted from the light source and is transmitted through the light-regulating film;
a memory that stores a measurement result measured by the light receiver, the measurement result including the intensity of the transmitted light; and
a processor that inspects a state of the inclined surface based on the measurement result.

2. The inspection device for a light-regulating film according to claim 1, wherein the light receiver is in a surface of a light incident surface of light which is incident on the light-regulating film from the light source and measures a polar angle of a central axis of the transmitted light, an intensity of which is the highest in the surface.

3. The inspection device for a light-regulating film according to claim 2, wherein the light receiver derives an inclination angle of the inclined surface with respect to the light incident end surface based on the polar angle of the central axis of the transmitted light.

4. The inspection device for a light-regulating film according to claim 2, wherein the light receiver is capable of moving within a range in which a polar angle $\theta$ made by a normal line direction of a light receiving surface of the light measurement means and a normal line direction of the base material satisfies $0° \leq \theta \leq 90°$.

5. The inspection device for a light-regulating film according to claim 2, wherein the light receiver is capable of moving in an azimuth angle direction viewed from a normal line direction of a principal surface of the base material.

6. The inspection device for a light-regulating film according to claim 2, wherein the light source is capable of moving.

7. The inspection device for a light-regulating film according to claim 6, wherein the light source is capable of moving in a manner to be linked with movement of the light receiver.

8. The inspection device for a light-regulating film according to claim 2, wherein the light receiver is fixed on a position on which a polar angle $\theta$ made by the normal line direction of the light receiving surface of the light receiver and the normal line direction of the base material becomes a specific angle within a range of $0° \leq \theta \leq 90°$.

9. The inspection device for a light-regulating film according to claim 1, further comprising:
a conveyor which conveys the light-regulating film in a direction parallel to the principal surface of the base material.

10. The inspection device for a light-regulating film according to claim 9, wherein the light source includes a plurality of light sources which are arranged with an interval in a direction orthogonal to a conveying direction of the light-regulating film conveyed by the conveyor.

11. The inspection device for a light-regulating film according to claim 10, wherein the light source includes a plurality of light sources which are arranged with an interval in a direction parallel to the conveying direction of the light-regulating film conveyed by the conveyor.

12. The inspection device for a light-regulating film according to claim 11, wherein the light receiver includes a plurality of light receivers which are provided in a manner to be associated with a plurality of light sources which are arranged with an interval in a direction parallel to the conveying direction.

13. The inspection device for a light-regulating film according to claim 10, wherein the light source includes a linear light source which emits linear light which extends in a direction orthogonal to the conveying direction of the light-regulating film conveyed by the conveyor.

14. The inspection device for a light-regulating film according to claim 10, wherein the light source includes a planar light source.

15. The inspection device for a light-regulating film according to claim 1, wherein the light receiver includes a controller that acquires positional information of a defective part of the light-regulating film, the defective part being detected in a case where an intensity of the transmitted light is measured.

16. The inspection device for a light-regulating film according to claim 1, wherein the light source is on the light diffusing portion side and makes light incident on the light-regulating film from the light diffusing portion side.

17. The inspection device for a light-regulating film according to claim 1, wherein the light source is on the base material side and makes light incident on the light-regulating film from the base material side.

18. The inspection device for a light-regulating film according to claim 1, wherein the light source is a high directivity light source.

19. A production device for a light-regulating film, comprising:
the inspection device for a light-regulating film according to claim 1.

20. A production device for a light-regulating film comprising:
an inspection device for the light-regulating film;
a plurality of processing devices which respectively perform mutually-different processing; and
a conveying device which conveys the light-regulating film in a middle of production among the plurality of processing devices,
wherein the inspection device comprises:
a light source which is on either one of a base material side and a light diffusing portion side and radiates light toward the light-regulating film, the light-regulating film including:
the base material having a light transmitting property, the light diffusing portion on a first surface of the base material, the light diffusing portion including a light emitting end surface on the base material side, a light incident end surface on a side opposite to the base material and has an area larger than an area of the light emitting end surface, and an inclined surface inclined with respect to the light emitting end surface, wherein a height from the light incident end surface to the light emitting end surface of the light diffusing portion is larger than a layer thickness of a light shielding portion, and the light shielding portion being provided in a region other than a region defining the light diffusing portion in the first surface, a light receiver on either the base material side or the light diffusing portion side not irradiated by the light source, the light receiver measuring an intensity of transmitted light that is emitted from the light source and is transmitted through the light-regulating film, a memory that stores a measurement result measured by the light receiver, the measurement result including the intensity of the transmitted light; and a processor that inspects a state of the inclined surface based on the measurement result, wherein the plurality of processing devices include an exposure device that defines the light diffusing portion which is made of photosensitive resin, an inspection result of the inclined surface, the inspection result being obtained by the inspection device, is fed back to an exposure amount of the exposure device, and the inspection device is in a middle of a conveying path of the light-regulating film in the conveying device.

* * * * *